United States Patent [19]
Bourguignon

[11] Patent Number: 6,068,681
[45] Date of Patent: May 30, 2000

[54] FILTERING DEVICE AND METHOD FOR NEUTRALIZING BAD SMELLS

[75] Inventor: Christiane Bourguignon, Aigremont, France

[73] Assignee: Deotech, France

[21] Appl. No.: 09/171,784

[22] PCT Filed: Apr. 25, 1997

[86] PCT No.: PCT/FR97/00749

§ 371 Date: Jun. 28, 1999

§ 102(e) Date: Jun. 28, 1999

[87] PCT Pub. No.: WO97/40863

PCT Pub. Date: Nov. 6, 1997

[30] Foreign Application Priority Data

Apr. 26, 1996 [FR] France .................................. 96 05326

[51] Int. Cl.[7] .................................................. B01D 53/04
[52] U.S. Cl. ................................ 95/116; 95/136; 95/141; 96/108; 96/153; 96/222
[58] Field of Search ................................. 55/524; 95/90, 95/92, 128, 136, 141, 142, 143, 116; 96/108, 121, 135, 153, 222, 290

[56] References Cited

U.S. PATENT DOCUMENTS

| | | | |
|---|---|---|---|
| 4,246,910 | 1/1981 | Rainer et al. | 96/153 X |
| 4,268,285 | 5/1981 | Mason | 96/222 |
| 4,272,261 | 6/1981 | Lynch, Jr. et al. | 96/222 |
| 4,306,892 | 12/1981 | Atalla et al. | 55/524 X |
| 4,534,775 | 8/1985 | Frazier | 55/524 X |
| 4,604,110 | 8/1986 | Frazier | 96/153 X |
| 4,689,058 | 8/1987 | Vogt et al. | 96/135 |
| 5,240,653 | 8/1993 | Ramkissoon | 96/222 X |
| 5,529,609 | 6/1996 | Gooch et al. | 96/153 X |
| 5,944,873 | 8/1999 | Jager et al. | 96/222 X |

FOREIGN PATENT DOCUMENTS

| | | |
|---|---|---|
| 5-154187 | 6/1993 | Japan . |
| WO86/05120 | 9/1986 | WIPO . |

Primary Examiner—Robert H. Spitzer
Attorney, Agent, or Firm—Larson & Taylor PLC

[57] ABSTRACT

The invention discloses a filtering device (1) for neutralizing volatile bad smells present in the atmosphere or carried by a flow of gas (5). The device comprises at least a layer (3) of natural zeolite material of set thickness impregnated with an aqueous solution with, for 100 parts by weight of zeolite, about 5 to about 20 parts by weight of the aqueous solution. This aqueous solution comprises for 1000 parts by weight of water, between about 1 part and about 20 parts by weight of a composite mixture comprising, for one part of ammonium ions or equivalent, one part of at least of one perfuming and/or deodorising composition.

9 Claims, 1 Drawing Sheet

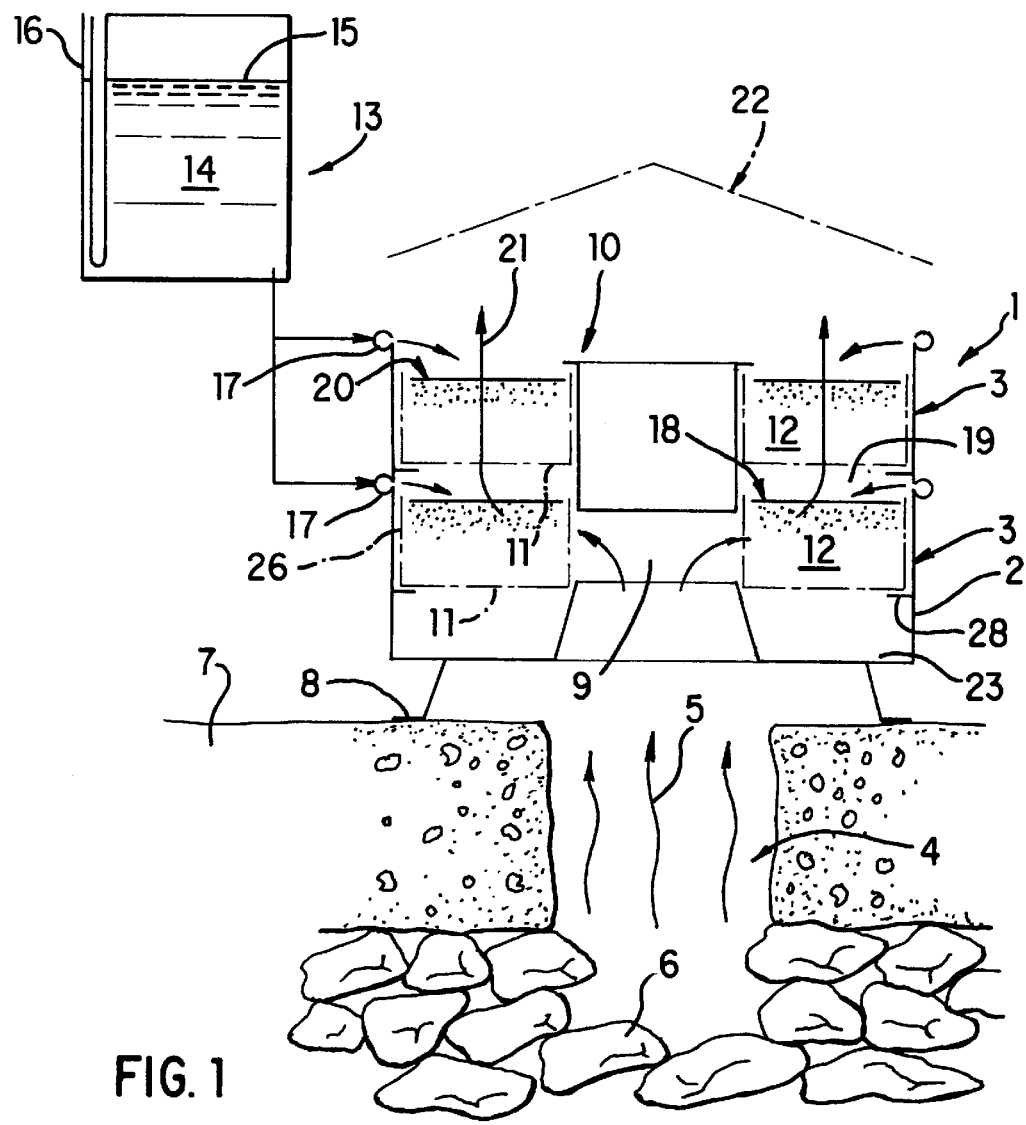
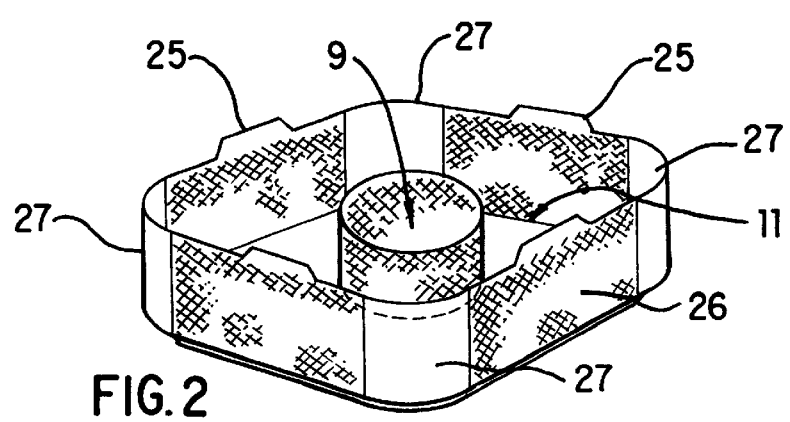
FIG. 1
FIG. 2

FILTERING DEVICE AND METHOD FOR NEUTRALIZING BAD SMELLS

The present invention relates to a filtration device for neutralizing the volatile unpleasant odors present in an atmosphere or conveyed by a stream of gas.

The invention also relates to a process using such a filtration.

The invention finds a particularly important, although not exclusive, application in the field of treating unpleasant odors such as body odors in bathrooms or in hairstyling salons, kitchen odors and tobacco odors, as well as particularly tenacious odors such as those of excrement or the odors of decomposing materials in public refuse sites.

The invention is also applicable to odors from factory chimneys, from purification plants and more generally to any malodorous gaseous effluent arising from industrial, commercial or residential sites.

Various methods and devices for treating unpleasant odors are already known.

A first technique consists in overcoming these odors by masking, either quantitatively by perfuming the atmosphere with a large amount of a more pleasant aromatic product, or by binding the malodorous molecules, in general by complexing them with other molecules, to give a product which has a different and more pleasant aroma.

However, this masking technique has drawbacks, since such a superposition does not completely eliminate the unpleasant odors, in particular given the very great sensitivity of human olfactory nerves.

For example, man remains sensitive to hydrogen sulfide even when its proportion in the atmosphere does not exceed 3 ppm.

Another technique envisaged is that of filtration.

This consists in reducing the unpleasant odors by filtering the odoriferous molecules during emission.

Thus, filters containing active charcoals which give acceptable results are known. However, since such filters cannot be absolute in practice, they allow malodorous molecules to pass through.

The present invention is directed toward providing a device and a process for treating unpleasant odors, which device and process are better than those previously known in terms of meeting the practical requirements, in particular as regards allowing better air purification in a simple, effective and inexpensive manner.

By using, in combination, mechanical filtration, with adsorption of the malodorous molecules, and release of perfuming molecules and/or of a composition of these pleasant-smelling molecules, the atmosphere or the stream of malodorous gas treated are thus purified and pleasantly perfumed.

With this aim, the invention proposes essentially a filtration device for neutralizing the volatile unpleasant odors present in an atmosphere or conveyed by a stream of gas, characterized in that it includes at least one layer of material made of natural zeolite of determined thickness, said layer being impregnated with an aqueous solution, with, per 100 parts by weight of zeolite, about 5 to about 20 parts by weight of said aqueous solution, said aqueous solution comprising, per 1000 parts by weight of water, between about 1 part and about 20 parts by weight of a composite mixture comprising, per one part of ammonium ions or equivalent, one part of at least one composition of perfuming and/or deodorizing nature.

The thickness of the layer is determined in a manner within the capability of those skilled in the art, as a function of the specific use of the filter depending on the characteristics of the filtered, gas, i.e. essentially the average flow rate of the malodorous molecules passing through the filter.

The adsorbing nature of the natural zeolite, the humidification of the atmosphere achieved by means of this filter appropriately impregnated with water and renewed over time, as well as the possibilities of release of perfuming and/or deodorizing molecules into the stream of filtered gas or into the filtered atmosphere, thus allow excellent physicochemical purification.

In advantageous embodiments, use is furthermore made of one and/or other of the following provisions:

the aqueous solution is cationic;

the aqueous solution comprises between about 3 parts and about 10 parts of composite mixture;

the layer made of natural zeolite is formed of granular material, with an average particle size of between about 0.1 cm and about 5 cm;

the composition of perfuming and/or deodorizing nature comprises an amount, which is effective for neutralizing the unpleasant odors, of a solvent represented by the following structural formula:

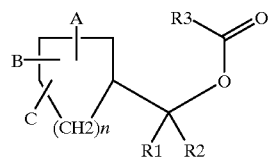

in which n is an integer from 2 to 4, A, B and C each independently represent hydrogen, a lower alkyl group containing 1 to 5 carbon atoms or a lower alkenyl group containing 3 to 5 carbon atoms, on condition that when two of the groups, A, B and C, are alkyl or alkenyl groups, they are attached to different carbon atoms and provided that the sum of the carbon atoms in A, B and C is not greater than 7, R1 and R2 each independently represent hydrogen or a lower alkyl group containing 1 to 5 carbon atoms, in which R1 and R2 together represent CH2m in which m is an integer from 2 to 6, R3 represents hydrogen or a lower alkyl or alkenyl group containing up to 6 carbon atoms, provided that the sum of the greatest number of carbon atoms in R1 or R2 plus R3 is not greater than 10.

Such compounds used in solvent form have molecules which are partly hydrophilic and partly hydrophobic, which have shown, unexpectedly, during tests carried out, that they improve the mechanism of impregnation of the zeolite and of release of the perfuming and/or deodorizing composition;

the composition of perfuming and/or deodorizing nature is produced from aromatic esters and/or from a complex aldehyde formation;

the composition of perfuming nature comprises a first aldehyde chosen from acyclic and non-terpenic aliphatic aldehydes, alicyclic non-terpenic aldehydes, terpenic aldehydes, aliphatic aldehydes substituted with an aromatic group and biofunctional aldehydes and/or a second aldehyde chosen from aldehydes containing unsaturation α to the aldehyde function conjugated with an aromatic ring and aldehydes whose function is borne by an aromatic ring;

the natural zeolite comprises at least one type of zeolite chosen from clinoptilotite, mordenite, chabazite, erionite, phillipsite, heulandite and analcime, and/or originating from any lithium-bearing deposit of material of zeolite type comprising physicochemical characteristics showing qualities equivalent to those of the materials mentioned above, of adsorption, of catalysis and of exchange, the device comprises means for forced circulation of the stream of gas through the layer of material in the device.

The invention also proposes a process for treating the volatile unpleasant odors present in an atmosphere or conveyed by a stream of gas, characterized in that the atmosphere or the stream of gas is treated by filtration with a filter composed of a layer of material made of natural zeolite of determined thickness impregnated with an aqueous solution, with, per 100 parts by weight of zeolite, about 5 to about 20 parts by weight of said aqueous solution, said aqueous solution comprising, per 1000 parts by weight of water, between about 1 part and about 20 parts by weight of a composite mixture comprising, per one part of ammonium ions or equivalent, one part of at least one composition of perfuming and/or deodorizing nature.

Advantageously, forced circulation of the atmosphere or of the stream of gas through the filter is carried out by sucking the atmosphere or the stream of gas through the filter.

The invention will be understood more clearly on reading the description which follows of specific embodiments, given by way of non-limiting example.

FIG. 1 schematically shows an embodiment of the device according to the invention arranged above a stream of gas to be deodorized.

FIG. 2 is a schematic view of a layer of zeolite material according to the invention. The structure is, for example, metallic, painted, of more or less cylindrical external shape.

FIG. 1 schematically shows a removable filtering device or filter 1, comprising a structure 2 for supporting two horizontal circular layers 3, for example identical layers, made of granular material based on zeolite according to the invention.

The layers are of determined thickness, for example each is 5 cm in thickness.

The filter 1 is placed above a well 4 for evacuation of decomposition gases 5 charged with unpleasant odors arising from storing rotting waste 6, which is incidentally covered with a layer of earth 7.

The external dimension of the filter and the outside diameter of the circular layers depends on the width of the well 4.

The supporting structure 2 rests on the edge of the well via a conical support 8 allowing the approximately leaktight conveyance of the gases, which rise here by natural extraction, and their passage through the filter.

This filter comprises a central chimney 9 which is cylindrical in the top part, closed off, for example, at mid-height of the filter, with a conical seat at the bottom part allowing the gases to be guided.

The chimney 9 is open-worked or railed in on the side walls 10 of its cylindrical top part so as to allow the passage of the gases radially toward the outside and through the walls of said chimney, in order to penetrate into the lower layer 3 of the filter, which it then crosses vertically, as well as the upper layer 3.

Each layer (see FIG. 2) rests on a sieve in the shape of a metal washer 11, for gravitational support of the granular material 12, compacted and humidified with a composite mixture according to the invention.

The layers of zeolite are humidified, for example, via a dropwise gravitational flow, from a tank 13 for storing the composite mixture 14, whose level 15 is checked regularly, for example via a visual indicator 16.

More specifically, the tank 13 feeds, for example, two manifolds 17 with evenly spaced suction nozzles, each of said manifolds being located at the periphery or in the center, above the upper circular surface of a corresponding layer.

In order to allow installation of the manifold for the lower layer, the upper surface 18 of this layer emerges into a circular space 19, which is closed on its walls, separating the two layers.

The upper surface 20 of the upper layer emerges into the open air in order to release the purified and/or perfumed gases 21.

A roof 22 for protecting against bad weather, for example in the form of a Chinese hat represented as a mixed line in FIG. 1, is moreover provided.

Lastly, the base of the structure 2 is formed by a circular tank 23 for holding the composite mixture which has not been absorbed by the zeolite. It is bounded on one side by the lower conical seat of the chimney 9 and on the other side by the outer wall of the structure.

If overfilled, the composite mixture impregnates the lower face of the lower layer 3, and runs off via the overspill in the chimney 9 toward the well 4.

The filter 1 can be fully dismantled, for example from the top, thereby allowing the layers 3 of zeolite to be replaced.

To do this, handles 25 for holding the layers 3 are provided, each being inserted into a cohesion envelope 26 with reinforced corners 27.

The envelope 26 is designed to rest on stops 28 fixed to the inner walls of the structure 2.

This results in great simplicity, robustness and particularly noteworthy reliability with regard to carrying out filter maintenance.

In general, as regards the composite mixture, as compounds which may be suitable according to the invention, mention will be made of the compounds chosen from the following:

aliphatic alcohols, advantageously C10 to C12 alcohols, such as decanol, citronellol and geraniol;

aldehydes, advantageously C10 to C13 aldehydes, which are either aliphatic, such as normal or branched dodecanal and myrac aldehyde, or are aromatic, such as cyclamen aldehyde, helional, heliotropin, para-methylphenylacetaldehyde and vanillin and its derivatives;

aliphatic ketones, advantageously C13 and C14 ketones, such as α- and β-ionones and damascones, as well as aliphatic and aromatic ketones with a musk odor which can contain up to 18 carbon atoms;

aliphatic esters, advantageously C8 and C15 esters, such as methyl dihydrojasmonate, methyl jasmonate, methyl cinnamate and ethyl methylphenylglycidate, and aromatic esters such as methyl anthranilate, methyl N-methylanthranilate, p-cresyl phenylacetate and amyl salicylate;

aromatic lactones such as coumarin and dihydrocoumarin and aliphatic lactones such as δ-decalactone, dodecalactone and undecalactone;

phenols such as eugenol and isoeugenol;

aromatic ethers such as diphenyl oxide naphthol methyl and ethyl ethers, and galaxolide;

nitrogenous compounds, for instance amines such as indole and its compounds of reaction with hydroxycitronellal, referred to as indoline, and aliphatic nitriles such as tridecene-2-nitrile;

aromatic amines, including pyridine derivatives, such as 2-(2'-methyl-2'-pentenyl)-5-methylpyridine.

Among the compounds mentioned above which are suitable according to the invention, mention will preferably be made of coumarin, allylionone, eugenol, isoeugenol, methyl dihydrojasmonate, indole, indolene, helional, α-ionone, β-ionone and 2-(2'-methyl-2'-pentenyl)-5-methylpyridine.

Those compounds which are liquid can be used just as they are. On the other hand, the crystalline compounds will be used after they have been dissolved in their usual solvent well known in perfumery, such as ethyl phthalate, benzyl benzoate, ethyl citrate and the like.

In addition, if so desired, the compounds according to the invention can also be used as a mixture in variable proportions giving a formulation which has virtually no unpleasant olfactory effect.

However, there is nothing to prevent one from adding to the compounds according to the invention, taken alone or as mixtures, and as desired, other perfuming starting materials which enhance the olfactory effect of the formulation to be applied for the user and for the environment.

In order to better illustrate the advantageous results obtained with the process according to the invention, two examples are given below, without any limitation whatsoever implied.

The test used is carried out with a panel of at least 50 people, at least five of whom are olfaction specialists, the others being selected without any particular criterion.

The effluent to be treated is defined in the following way:
For a quantifiable and isolated effluent, for example H2S:
by physical reduction:
By measuring its concentration in air before treatment and its concentration in the filtered air,
by sensitive reduction:
To do this, the sensations perceived by inhaling, by means of an olfactometer or a beaker test:
the air treated with the filtration system and impregnated with deodorizing solution,
two "decoy" samples, one perfumed and the other malodorous,
air artificially charged with an H2S concentration identical to that of the treated air, without deodorizing solution, are graded on a scale of intensity by the entire panel.

In the case of a malodorous effluent of complex type, for example one arising from an organic degradation, the sensations perceived by inhaling, by means of an olfactometer or a beaker test:
the air treated with the filtration system and impregnated with deodorizing solution,
two "decoy" samples, one perfumed and the other malodorous of another nature,
a sample of unperfumed air charged with $H^2S$, at the residual concentration recorded for treated air, are graded on a scale of intensity by the entire panel.

In all the cases, the panel members grade their sensations on two graduated scales (A and B) by distinguishing the intensity of the unpleasant odor (scale —A—) and the total intensity of the odor (scale —B—).

Given the temporary anosmia which is induced by this technique, it is recommended to wait at least one minute between two samples. This waiting period can be filled, either by a question of control or by smelling or tasting an entirely different product (eau de toilette, chewing-gum).

The original odor receives a value of 0 on the graduated scales.

For each scale, the graduation ranges, in steps of 5, from −20 to +20, the grade −20 representing absolute neutrality and the absence of any olfactory sensation.

The results are obtained by taking the average, for each scale, of the grades assigned by the panel members.

Scale A:
An average below 0 reflects a reduction in the unpleasant odor, an average above 0 reflects an increase in the unpleasant odor.

Scale B:
An average below 0 reflects a reduction in the intensity of the odor perceived, an average above 0 reflects an increase in the intensity of the odor perceived.

The results are then analyzed according to the following criteria:
An average A above 0, with an average above 0 reveals a masking effect,
an average A below 0, with an average above 0 reveals an inhibition-reduction effect.

Given the residual traces of malodorous effluents and of perfuming molecules, it is considered that the optimum result is in the range −5/−10 for Scales A and B.

Test 1:
Air charged with 40 ppm of H2S at 20° C.
Zeolite filter granules of 0.8/1.2 cm
Clinoptinolite
Thickness: 40 mm
Soaked with 15% by weight of an aqueous composite solution based on ammonium ions, esters, aldehydes and solvents, of the type known under the name Vailex sold by the company Bush Boake Allen, at a concentration of 5 per 1000.
Air flow rate: 0.04 m/second
Results observed:
a) Measurement of the H2S concentration after filtration: 7 ppm
b) residual odor—control sample: air +7 ppm H2S, corresponding to the 0 value of scales A and B
panel result for the residual odor: Scale A: −6 and Scale B: −5

Test No. 2:
Strong odor of organic decomposition (sample taken from a refuse site)
Presence of Bio-gas, methane, mercaptans, H2S, NH3, etc.
Zeolite filter granules of 0.8/1.2 cm
50% clinoptilite—50% chabazite
Thickness: 30 mm
Soaked with 15% by weight of an aqueous composite solution based on ammonium ions, esters, aldehydes and solvents, of the type known under the name Vailex, at a concentration of 4 per 1000.
Air flow rate: 0.1 m/second
Panel result for the residual odor: Scale A: −8 and Scale B: −6.

As goes without saying and as can be seen from the above, the present invention is not limited to the embodiment described more particularly. Rather, it embraces all the variants and in particular those in which the filter comprises means for generating forced circulation, those in which it comprises only one layer or several layers of zeolite-based material and those in which the humidification system is different.

What is claimed is:
1. Process for treating the volatile unpleasant odors present in an atmosphere or conveyed by a stream of gas, in which process the atmosphere or the stream of gas is treated by filtration with a filter composed of a layer of adsorbent material of determined thickness impregnated with an aqueous solution, with, per 100 parts by weight of material, about

5 to about 20 parts by weight of said aqueous solution, characterized in that the material is natural zeolite comprising at least one material chosen from clinoptilotite, mordenite, chabazite, erionite, phillipsite, heulandite and analcime,
said aqueous solution comprising, per 1000 parts by weight of water, between about 1 part and about 20 parts by weight of a composite mixture comprising, per one part of ammonium ions or equivalent, one part of at least one composition of perfuming and/or deodorizing nature.

2. Process according to claim 1, characterized in that forced circulation of the atmosphere or of the stream of gas through the filter is carried out by sucking said atmosphere or said stream of gas through said filter.

3. Filtration device (1) for neutralizing the volatile unpleasant odors present in an atmosphere or conveyed by a stream of gas (5), this device comprising at least one layer (3) of adsorbent material (12) of determined thickness impregnated with an aqueous solution (14), with, per 100 parts by weight of material, about 5 parts to about 20 parts by weight of said aqueous solution, characterized in that the material is natural zeolite comprising at least one material chosen from clinoptilolite, mordenite, chabazite, erionite, phillipsite, heulandite and analcime,
in that the device comprises humidification means and in that said aqueous solution is cationic and comprises, per 1000 parts by weight of water, between about 1 part and about 20 parts by weight of a composite mixture comprising, per one part of ammonium ions or equivalent, one part of at least one composition of perfuming and/or deodorizing nature.

4. Device according to claim 3, characterized in that the aqueous solution comprises between about 3 parts and about 10 parts of composite mixture.

5. Device according to claim 3, characterized in that the layer (3) made of natural zeolite is formed of granular material with an average particle size of between about 0.1 cm and about 5 cm.

6. Device according to claim 3, characterized in that the composition of perfuming and/or deodorizing nature comprises an amount, which is effective for neutralizing the unpleasant odors, of a compound represented by the following structural formula:

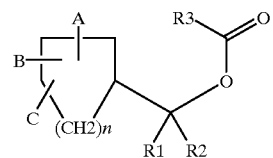

in which n is an integer from 2 to 4, A, B and C each independently represent hydrogen, a lower alkyl group containing 1 to 5 carbon atoms or a lower alkenyl group containing 3 to 5 carbon atoms, on condition that when two of the groups, A, B and C, are alkyl or alkenyl groups, they are attached to different carbon atoms and provided that the sum of the carbon atoms in A, B and C is not greater than 7, R1 and R2 each independently represent hydrogen or a lower alkyl group containing 1 to 5 carbon atoms, in which R1 and R2 together represent CH2m in which m is an integer from 2 to 6, R3 represents hydrogen or a lower alkyl or alkenyl group containing up to 6 carbon atoms, provided that the sum of the greatest number of carbon atoms in R1 or R2 plus R3 is not greater than 10.

7. Device according to claim 3, characterized in that the composition of perfuming and/or deodorizing nature is produced from aromatic esters and/or from a complex aldehyde formation.

8. Device according to claim 7, characterized in that the perfuming composition comprises a first aldehyde chosen from acyclic and non-terpenic aliphatic aldehydes, alicyclic non-terpenic aldehydes, terpenic aldehydes, aliphatic aldehydes substituted with an aromatic group and biofunctional aldehydes and a second aldehyde chosen from aldehydes containing unsaturation α to the aldehyde function conjugated with an aromatic ring and aldehydes whose function is borne by an aromatic ring.

9. Device according to claim 3, characterized in that it also comprises means for forced circulation of the stream of gas through the layer of material in the device.

* * * * *